US006432925B1

(12) United States Patent
Hoon et al.

(10) Patent No.: US 6,432,925 B1
(45) Date of Patent: Aug. 13, 2002

(54) RNA CANCER VACCINE AND METHODS FOR ITS USE

(75) Inventors: Dave S. B. Hoon, Los Angeles, CA (US); Yasufumi Kaneda, Osaka (JP)

(73) Assignee: John Wayne Cancer Institute, Santa Monica, CA (US)

( * ) Notice: Subject to any disclaimer, the term of this patent is extended or adjusted under 35 U.S.C. 154(b) by 0 days.

(21) Appl. No.: 09/061,794

(22) Filed: Apr. 16, 1998

(51) Int. Cl.$^7$ .................. A61K 48/00; A61K 39/12; A61K 9/127; C12N 15/74; C07H 21/04

(52) U.S. Cl. ............... 514/44; 435/320.1; 536/23.1; 424/199.1; 424/450

(58) Field of Search .............. 514/44; 424/199.1, 424/450; 536/23.1; 435/320.1

(56) References Cited

U.S. PATENT DOCUMENTS 5,631,237 A  5/1997  Dzau et al. ............ 514/44

FOREIGN PATENT DOCUMENTS

FR  2 676 072 A  11/1992

OTHER PUBLICATIONS

Restifo et al. (1993) J. Immunother., vol. 14, 182–190.*
Yasutomi et al. (1995) J. Virol., vol. 69 (4), 2279–2284.*
Saekl et. al., Development and haracerization of Cationic Liposomes Conjugated with HVJ(Sendai Virus): Reciprocal Effect of Cationic Lipid for In Vitro and In Vivom Gene Transfer, 1997; Human Gene Therapy 8: 2133–2141.*
Ellison et. al.; Fusigenic Liposome–mediated DNA Transfer into Cardiac Myocytes, 1996, J. Mol Cell Cardiol 28: 1385–1399.*
The Journal of Investigative Dermatology; Abstract.*
*Okamoto, T., et al., "Induction of Antibody Response To Human Tumor Antigens By Gene Therapy Using a Fusigenic Viral Liposome Vaccine," Gene Therapy, (Sep. 1997), 4(9), pp. 969–679.
International Search Report, Oct. 25, 1999.
Dzau, Victor J. et al., "Fusigenic Viral Liposome for Gene Therapy in Cardiovascular Diseases," Proc. Natl. Acad. Sci USA, vol. 93 (Oct. 1996); pp. 11421–11425.
Hoon et al., "Current Status of Human Melanoma Vaccines: Can They Control Malignant Melanoma?," BioDrugs, 7:1, (Jan. 1997), pp. 66–84.
Isaka, Yoshitaka et al., "Gene Therapy by Skeletal Muscle Expression of Decorin Prevents Fibrotic Disease in Rat Kidney," Nature Medicine, 2:4 (Apr. 1996), pp. 418–423.
Kaneda Y. et al., "Increased Expression of DNA Cointroduced with Nuclear Protein in Adult Rat Liver," J. Mol. Med., 73, (1995), pp. 289–297.
Nakamura, Norimasa et al., "Transient Introduction of a Foreign Gene into Healing Rat Patellar Ligament," J. Clin. Invest., The American Society for Clinical Investigation, Inc., vol. 97: (Jan. 1996), pp. 226–231.

Okamoto, T., et al., "Induction of Antibody Response to Human Tumor Antigens by Gene Therapy Using a Fusigenic Viral Liposome Vaccine," Gene Therapy, 4 (1997), pp. 969–976.

Wickelgren, Ingrid, "Cancer Vaccines," Popular Science, (Jan. 1998), pp. 62–68.

Yanagihara, I. et al., "Expression of Full–Length Human Dystrophin cDNA in mdx Mouse Muscle by HVJ–liposome Injection," Gene Therapy, 3 (1996), pp. 549–553.

Fukashi, Doi et al. "Detection of beta–human chorionic gonadotropin mRNA as a marker of cutaneous malignant melanoma," Database Biosis [Online] PREV 1996 98 69 82 66 XP002143229, Abstract.

Kawakami, Yutaka et al., "Cloning of the gene coding for a shared human melanoma antigen recognized by autologous T cells infiltrating into tumor," Proc. Nat'l. Acad. Sci. USA, vol. 91, pp. 3515–3519, Apr. 1994.

Sarantou, Terry et al., "Melanoma–associated Antigens as Messenger RNA Detection Markers for Melanoma," Cancer Research, 57, pp. 1371–1376, Apr. 1, 1997.

Sensi, Marialuisa et al., "Cytotoxic T–lymphocyte clones from different patients display limited T–cell–receptor variable–region gene usage in HLA–A2–restricted recognition of the melanoma antigen Melan–A/MART–1," Proc. Nat'l Acad. Sci USA, vol. 92, pp. 5674–5678, Jun. 1995.

Suzuki, Ken, et al., "In Vivo Gene Transfection with Heat Shock Protein 70 Enhances Myocardial Tolerance to Ischemia–Reperfusion Injury in Rat," J. Clin. Invest., vol. 99, No. 7, Apr. 1997, pp. 1645–1650.

Tuting, Thomas et al, "Autologous Human Monocyte–Derived Dendritic Cells Genetically Modified to Express Melanoma Antigens Elicit Primary Cytotoxic T Cell Response In Vitro: Enhancement by Cotransfection of Genes Encoding the Th 1–Biasing Cytokines IL–12 and IFN–α," J. of Immun., vol. 160, No. 3, Feb. 1, 1998, pp. 1139–1147.

(List continued on next page.)

Primary Examiner—A. M. S. Beckerleg
(74) Attorney, Agent, or Firm—McCutchen, Doyle, Brown & Enersen, LLP

(57) ABSTRACT

RNA cancer vaccines and methods for their use are described. The vaccines are comprised of viral liposomes comprising nucleic acid, preferably RNA, encoding a tumor-associated antigen. The viral liposomes may be formed by the fusion of HVJ reagents with nonviral reagents. The vaccine may be administered subcutaneously, intradermally, intramuscularly or into an organ. The vaccine may be administered to induce a host normal cell to express the tumor associated antigen.

87 Claims, 6 Drawing Sheets

OTHER PUBLICATIONS

Wolfe, Thomas et al., "Two tyrosinase nonapeptides recognized on HLA–A2 melanomas by autologous cytolytic T lymphocytes," *Eur. J. Immunol.,* 1994, 24: pp. 759–764.

Yoshina, Ichiro et al., "Human Tumor–Infiltrating CD4+T Cells React to B Cell Lines Expressing Heat Shock Protein 70," *J. Immuno.,* vol. 153, No. 9, 1994, pp. 4149–4158.

International Search Report, mailed Oct. 8, 2000.

Martinon, Frederic, "Induction of virus–specific cytotoxic T lympocytes in vivo by liposome–entrapped mRNA," *Eur. J. Immunol.,* (1993) 23: pp. 1719–1722.

Kaneda, Yasufumi. et al., "The Improved Efficient Method for Introducing Macromolecules into Cells Using HVJ (Sendai Virus) Liposomes with Gangliosides," Experimental Cell Research, 173 (1987), pp. 56–69.

Otomo, Takanobu, et al., "EBV replicon vector system enchances transgene expression in vitro: applications to cancer gene therapy," The Journal of Gene Medicine, 2001; 3:345–352.

* cited by examiner

SEQUENCE LISTING

```
<160> NUMBER OF SEQ ID NOS: 6

<210> SEQ ID NO 1
<211> LENGTH: 54
<212> TYPE: DNA
<213> ORGANISM: Corynebacterium diptheriae
<220> FEATURE:
<223> OTHER INFORMATION: Sense oligonucleotide sequence derived from
      diptheria toxin fragment B nucleotide sequence

<400> SEQUENCE: 1
agcttacgca accatttctt catgacgggt atgctgtcag ttggaacact gttg          54

<210> SEQ ID NO 2
<211> LENGTH: 54
```

```
<212> TYPE: DNA
<213> ORGANISM: Corynebacterium diptheriae
<220> FEATURE:
<223> OTHER INFORMATION: Antisense oligonucleotide sequence derived from
      diptheria toxin fragment B nucleotide sequence

<400> SEQUENCE: 2
tcgacaacag tgttccaact gacagcatac ccgtcatgaa gaaatggttg cgta            54

<210> SEQ ID NO 3
<211> LENGTH: 16
<212> TYPE: PRT
<213> ORGANISM: Corynebacteriam diptheriae
<220> FEATURE:
<223> OTHER INFORMATION: C-terminal end of diptheria toxin fragment B

<400> SEQUENCE: 3

Thr Gln Pro Phe Leu His Asp Gly Tyr Ala Val Ser Trp Asn Thr Val
 1               5                  10                  15

<210> SEQ ID NO 4
<211> LENGTH: 20
<212> TYPE: PRT
<213> ORGANISM: Artificial Sequence
<220> FEATURE:
<223> OTHER INFORMATION: Diptheria toxin fragment B C-terminal peptide
      with a four histidine tag

<400> SEQUENCE: 4

Thr Gln Pro Phe Leu His Asp Gly Tyr Ala Val Ser Trp Asn Thr Val
 1               5                  10                  15

His His His His
            20

<210> SEQ ID NO 5
<211> LENGTH: 20
<212> TYPE: DNA
<213> ORGANISM: Artificial Sequence
<220> FEATURE:
<223> OTHER INFORMATION: PCR primer for MAGE-1

<400> SEQUENCE: 5
taatacgact cactataggg                                                  20

<210> SEQ ID NO 6
<211> LENGTH: 20
<212> TYPE: DNA
<213> ORGANISM: Artificial Sequence
<220> FEATURE:
<223> OTHER INFORMATION: PCR primer for MAGE-1

<400> SEQUENCE: 6
aggggcaaac aacagatggc                                                  20
```

RNA CANCER VACCINE AND METHODS FOR ITS USE

INTRODUCTION

1. Technical Field

This invention relates to the field of vaccines used as cancer therapy.

2. Background

A vaccine is one of the most efficacious, safe, nontoxic and economical weapons to prevent disease and to control the spread of disease. Conventional vaccines are a form of immunoprophylaxis given before disease occurrence to afford immunoprotection by generating a strong host immunological memory against a specific antigen. The primary aim of vaccination is to activate the adaptive specific immune response, primarily to generate B and T lymphocytes against specific antigen(s) associated with the disease or the disease agent.

Similarly, cancer vaccines aim to generate immune responses against cancer tumor-associated antigens. Cancers can be immunogenic and can activate host immune responses capable of controlling the disease and causing tumor regression. However, cancer at the same time can be specifically and nonspecifically immunosuppressive and can evade the host's immune system. Many protein/glycoprotein tumor-associated antigens have been identified and linked to certain types of cancer. MAGE-3, MAGE-1, gp100, TRP-2, tyrosinase, MART-1, β-HCG, CEA, Ras; B-catenin, gp43, GAGE-1, BAGE-1, PSA, MUC-1,2,3, and HSP-70 are just a few examples.

Multiple approaches are being assessed in immunizing cancer patients with tumor-associated antigens (TAAs). Vaccines in clinical use fall into several categories determined by their cellular components, which range from whole cells to immunogenic peptides. Whole cell and cell lysate vaccines can be autologous or allogeneic vaccines, depending on the host origin of the cancer cells. An autologous whole cell cancer vaccine is a patient-specific formulation made from the host's tumor. Autologous cancer vaccines generally are not clinically successful unless they are modified. Because they are patient-specific, they also are costly and limited to those patients from whom cancer cells can be obtained in sufficient quantity to produce a single-cell suspension. In addition, the inherently limited number of cells is problematic with respect to multiple vaccinations, making an autologous formulation impractical for prophylaxis or treatment of early disease. Some of these problems are solved with allogeneic whole cell vaccines or genetically engineered whole cell vaccines. However, these methods may be tedious and time consuming. In addition, genetically engineered whole cell vaccines must be tested for antigenicity and immunogenicity. Current animal tumor models are not truly representative of human cancer tumors.

Natural and recombinant cancer protein antigen vaccines are subunit vaccines. Unlike whole cell vaccines, these subunit vaccines contain defined immunogenic antigens at standardized levels. The key problem with such vaccines is finding the right adjuvant and delivery system. In addition, purification of natural or recombinant tumor antigens is tedious and not always logistically practical. Human cancer vaccines require culturing tumor cells, purifying tumor antigens, or producing specific peptides or recombinant proteins. In addition, there are problems related to antigen presentation and host major histocompatibility complex (MHC) polymorphism.

Vaccines which include nucleic acid encoding the tumor antigens rather than vaccines comprising the antigen itself address some of these problems. The host normal cells (nonhemopoietic) can express and present the tumor antigens to the immune system. In general, when a cytopathic virus infects a host normal cell, the viral proteins are endogenously processed and presented on the cell surface, or in fragments by MHC molecules. Foreign defined nucleic acid transfected and expressed by normal cells can mimic viral infections.

DNA vaccines recently have been shown to be a promising approach for immunization against a variety of infectious diseases. Michel, M L et al., Huygen, K, et al., and Wang, B, et al. Delivery of naked DNAs containing microbial antigen genes can induce antigen-specific immune responses in the host. The induction of antigen-specific immune responses using DNA-based vaccines has shown some promising effects. Wolff, J. A., et al. Recent studies have demonstrated the potential feasibility of immunization using a DNA-mediated vaccine for CEA and MUC-1. Conry, R. M., et al. and Graham, R. A., et al.

DNA-based vaccination has shown to have a greater degree of control of antigen expression, toxicity and pathogenicity over live attenuated virus immunization. However, although in vivo DNA vaccination protocols are available, improvements in in vivo delivery and transgene expression are needed. For example, introduction of DNA into specific cells often results in degradation of the DNA by endosomes or lysosomes. Vaccines that require the tumor antigen to be expressed by tumor cells may result in problems such as suppression of immune responses or altered physiologic functions that modify antigen expression because tumor cells have many negative type regulating elements. Current approaches of in vivo delivery of DNA by retroviral or adenoviral vectors have problems related to efficacy, viral gene integration, potential pathogenic activity and immune response to viral vector encoding proteins. In addition, the DNA in DNA vaccines may be incorporated into the host cell's DNA, making it difficult to halt production of the tumor antigen when treatment is complete. Some liposome delivery systems are undesirable because they may incorporate into hemopoietic-derived cells such as lymphocytes.

SUMMARY OF THE INVENTION

The invention provides methods and compositions for immunizing against a tumor-associated antigen, suppressing or attenuating tumor growth, and treating cancer. The methods and compositions provided may induce an antibody response through IgG, IgM, or IgA molecules, or a cell-mediated response through CD4, CD8 or other T cell subsets.

The compositions provided by the invention are comprised of viral liposomes comprising nucleic acid, preferably RNA, encoding a tumor-associated antigen. The viral liposomes may be formed by the fusion of HVJ reagents with nonviral reagents. The nucleic acid may be DNA or RNA. The tumor-associated antigen may be any antigen known to be associated with tumors, for example MAGE-1, MAGE-3, gp100, TRP-2, tyrosinase, MART-1, β-HCG, or HSP-70. The compositions of the antigens may be chimeric with other molecules that may include diphtheria toxin, other immunogenic toxin peptides or helper antigen peptides. The compositions may include other components, such as HMG-1, that direct the nucleic acid to a certain location in the cell or direct translation of the tumor-associated antigen.

The methods provided by the invention comprise administering a vaccine comprised of viral liposomes comprising nucleic acid encoding a tumor-associated antigen. The vaccine may be administered subcutaneously, intradermally, intramuscularly, or into an organ. The vaccine may be administered in a way that induces a host normal cell to express the tumor-associated antigen.

DEFINITIONS

HVJ means Hemagglutinating Virus of Japan.

Viral liposome means a hybrid vector of viral and non-viral reagents. Anionic or cationic liposomes are fused with virus, preferably HVJ (virus strain of paramyxovirus family).

DETAILED DESCRIPTION OF PREFERRED EMBODIMENTS

The invention provides novel efficient approaches using a viral liposome system to deliver tumor antigen nucleic acids in vivo to immunize the host. The invention avoids many of the tedious processes involved in vaccine preparation. Quality control and purity of plasmid DNA or RNA can be more easily monitored. Fusigenic viral liposomes can provide an efficient vehicle to package, deliver and direct nucleic acid to specific targets and at the same time protect against nucleic acid degrading enzymes in body fluids and cytoplasmic organelles. Tumor antigen is expressed on a background of normal cell(s) as opposed to a tumor cell. Nucleic acid vaccination provides an opportunity for molecular immuno-physiologic manipulation of antigen expression that can be a useful tool in cancer vaccine design. The vaccine provided by this invention does not incorporate into hemopoietic-derived cells as do other liposome delivery systems.

The invention provides methods and compositions for immunizing against a tumor-associated antigen, suppressing or attenuating tumor growth, and treating cancer. The methods and compositions provided may induce an antibody response (IgG, IgM, IgA) or a cell mediated response through CD4, CD8 or T cells.

Figure 1:
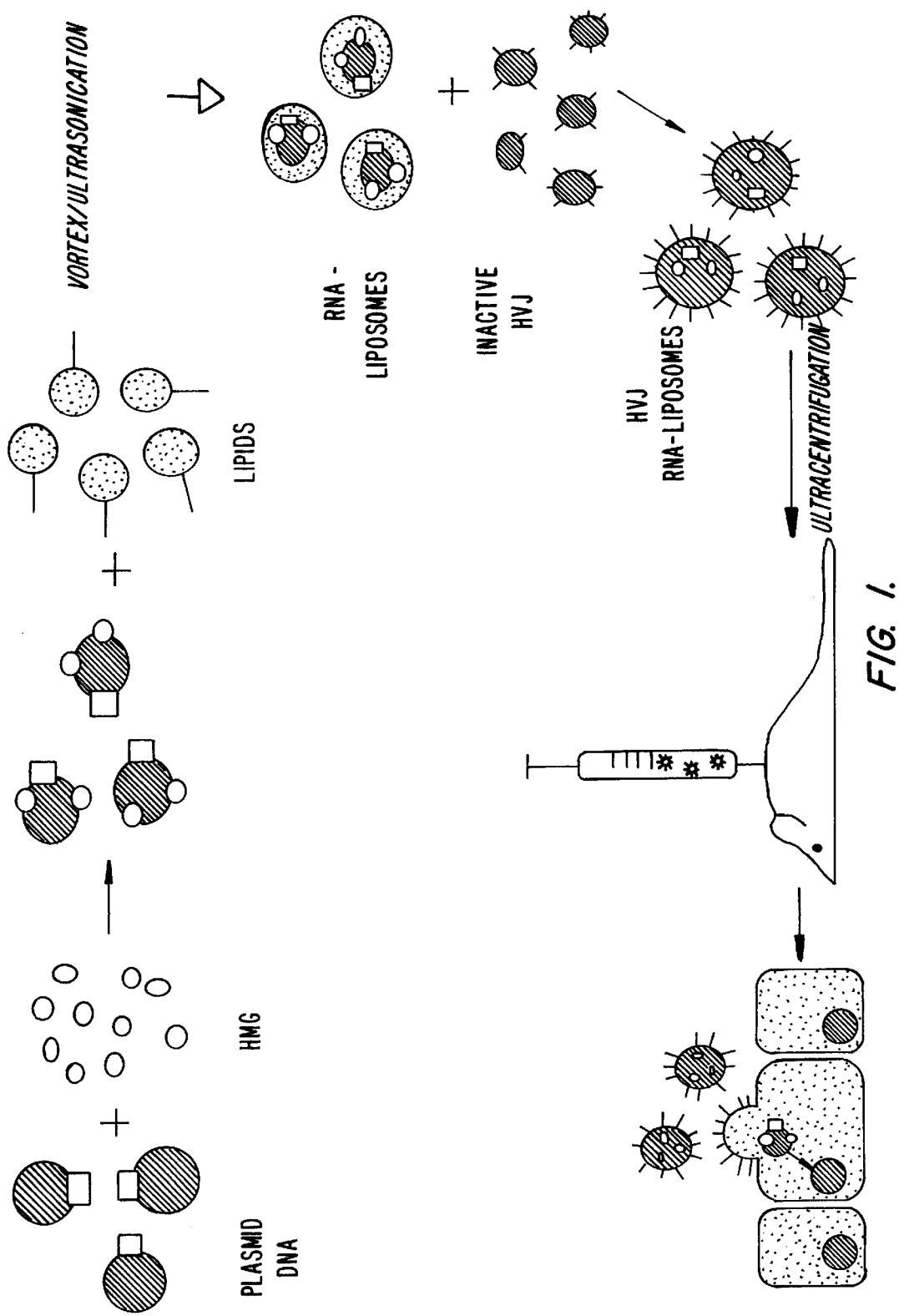
FIG. 1 is a schematic diagram of HVJ-liposome plus plasmid RNA preparation and immunization of mice.

The compositions provided by the invention are comprised of viral liposomes comprising nucleic acid, preferably RNA, encoding a tumor-associated antigen. A preferred method of producing the viral liposomes is to fuse anionic or cationic liposomes with an inactive virus, preferably HVJ as described in Dzau, et al. and U.S. Pat. No. 5,631,237. Another preferred method of preparing viral liposomes is described in Example 5, below. A schematic diagram of the production of viral liposomes is shown in FIG. 1. HVJ proteins are known for their fusing properties to cell membranes of nonhemopoietic nucleated cells. This hybrid vector allows targeting to normal nonhemopoietic cells and delivery of encapsulated nucleic acid into the cytoplasm of cells without lysosome-endosome degradation. The viral liposome system also can deliver nucleic acid and protein molecules together. In addition, purified or recombinant fusion polypeptides of HVJ rather than the entire viral envelope may be used.

Any number and combination of nucleic acid sequences encoding TAAs may be included in the vaccine. The MAGE gene family members are examples of TAAs that would be useful in the invention. MAGE-1, MAGE-2, and MAGE-3 antigens were first described in melanoma and subsequently demonstrated in various other cancers. MAGE-1 and MAGE-3 genes are expressed in greater than 30 percent of melanomas and carcinomas such as lung, breast, liver and gastrointestinal cancers, but not in normal tissues except testes. The MAGE-1 and MAGE-3 antigens have been shown to be immunogenic, expressed by a wide variety of human cancers and not expressed by normal tissues. These factors are important in the overall design of an effective vaccine against multiple cancers.

There are other MAGE gene family members with similar homologies. De Plaen, E, et al. The strategy of using two dominant immunogenic MAGE family antigens may be beneficial in that they can elicit immunity to a wide spectrum of MAGE antigens expressed by different human tumors. Vaccination with MAGE-1 and MAGE-3 could induce immune responses to tumors expressing either antigen because of the cross-reactivity between MAGE-1 and MAGE-3. This property is useful because MAGE-1 and MAGE-3 are not always co-expressed in the same tumor biopsy or cell lines.

Nucleic acid sequences encoding many other TAAs will be useful in the vaccines provided by the invention. B-catenin, TRP-2, TRP-1, gp100 p17 mel, MART-1, GAGE-1, BAGE-1, HSP-70, gp43, β-HCG, Ras mutation, MUC-1, 2, and 3, PSA, p53 mutation, HMW, MUC-18, HOJ-1, tyrosinase, and carcinoembryonic antigen (CEA) are examples. In general, any antigen that is found to be associated with cancer tumors may be used. See Gomella, et. al., Gerhard, et al., Zhang, et al., Nollau, et al., Mivechi, et al., Ralhan, et al., Yoshino, et al., Shirasawa, et al., Cheung, et al., Sarantou, et al., Doi, et al., Hoon, et al. (1997), Eynde, et al., Hoon, et al. 1996), Takahashi, et al., Kawakami, et al., Wolfel, et al., Vijayasaradhi, et al., Yokoyama, et al., Kwon, and Sensi, et al.

Multiple genes can be incorporated into the vaccine to produce a polyvalent DNA or RNA cancer vaccine. Effective tumor vaccination may require a polyvalent antigen vaccine to control human tumor progression effectively. Nucleic acids encoding these antigens can be incorporated into the vaccine provided by this invention.

RNA encoding TAAs can be used in the vaccines of the invention when fast, short-term expression of the antigen is desired. Because RNA will not incorporate into the cellular chromosomes, using RNA vaccines also eliminates the possibility that antigens will continue to be expressed when the treatment is no longer desired. RNA also has a more limited biological life when compared to DNA resulting in less danger of virulence to host cells and greater control of expression. In addition, in RNA vaccines, the antigen to be expressed is translated directly from the RNA, eliminating the uncertainty that arises during the transcription of DNA in DNA vaccines.

A drug sensitive gene can be incorporated into the RNA vector to turn off protein expression at any time in vitro. Example of drug sensitive genes are tetracycline, ampicillin, gentamycin, etc.

An immunogenic determinant, such as Diphtheria toxin, also may be included as a "helper" antigen on the TAA to improve its efficacy. Diphtheria toxin B fragment COOH—terminal region has been shown to be immunogenic in mice. Autran, B., et al. HSP70, in part or in whole, as well as other immunogenic peptides, such as influenza viral or immunogenic sequences peptide with an anchoring motif to HLA class I and class II molecules, also may be included in the vaccines of the invention.

The compositions may include other components to serve certain functions, for example, directing the nucleic acid to a certain location in the cell or directing transcription of the tumor-associated antigen. Compositions for transport to the nucleus may be included, particularly members of the high mobility group (HMG), more particularly HMG-1, which is a non-histone DNA-binding protein. In combination with antisense molecules, RNAses such as RNAseH, may be used, which degrade DNA-RNA hybrids. Other proteins which will aid or enhance the function of the TAA may be included, such as peptide sequences that direct antigen processing, particularly HLA presentation, or movement in the cytoplasm.

The vaccine provided by this invention may be administered subcutaneously, intramuscularly, intradermally, or into an organ. Intramuscular injection has been shown in the past to be an important delivery route for induction of immunity. Skeletal muscle has properties such as high vascularization and multi-nucleation. In addition, it is nonreplicating and capable of expressing recombinant proteins. These properties are advantageous for gene therapy. One theory of the mechanism of how muscle presents the protein and induces immune response is that recombinant protein is produced and released into the vascular network of the muscle and eventually presented by professional antigen-presenting cells such as dendritic cells or macrophages infiltrating the muscle. Another suggestion is that at the injection site muscle injury induces myoblast proliferation and activation of infiltrating macrophages or dendritic-like cells, and they then present antigens through MHC class II antigen. Thus, other tissues which have similar qualities also would be good delivery sites for the vaccine.

The chosen route of administration will depend on the vaccine composition and the disease status of patients. Relevant considerations include the types of immune cells to be activated, the time which the antigen is exposed to the immune system and the immunization schedule. Although many vaccines are administered consecutively within a short period, spreading the immunizations over a longer time may maintain effective clinical and immunological responses.

In determining immunization scheduling for cancer vaccines, the following questions should be considered with regard to individualizing vaccine protocols:

Are multiple immunizations over a short period of time better than over a long period of time to induce long term effective immunity?

If the patient develops a tumor recurrence should the vaccination protocol be changed?

Does excessive immunization induce immune suppression or tolerance?

Should immunization schedules differ among individuals with different clinical stages of disease?

An example of an administration schedule is to administer vaccines by injection at weeks 0, 2, 4, 8, 12, 16, and every fourth week successively for 1 year. After that, patients are placed on a 3- to 6- month vaccine schedule for several years. A preventative immunization schedule may consist of three immunizations, one every three to four weeks. Treatment after removal of a tumor may consist of immunization every week for one month.

Unlike most non-neoplastic diseases treated with vaccines, an actively growing cancer is a dynamic biological entity that is genetically and phenotypically continuously evolving. A tumor that is allowed to evolve genetically and phenotypically will eventually become more difficult for the host immune system to control. However, cancer vaccines may be more effective when combined with other adjuvant therapies such as chemotherapies, or other immunotherapies such as monoclonal antibodies and cytokines. A more aggressive treatment regimen approach at early stages of tumor development may be more effective in preventing the evolution of escape mechanisms. A more aggressive treatment also may be necessary for cancers that are highly malignant versus relatively benign cancers with a low risk of recurrence. In general, if the host has a weak immune response to the vaccination, then a larger dose or a more frequent vaccination should be given.

The present invention allows repeated administration of the vaccine because injection of HVJ-liposomes produces levels of antibody not sufficient to neutralize further vaccination by HVJ-liposomes. In addition, cytotoxic T-cells against HVJ are not generated.

EXAMPLE 1

Vaccination of Mice with Viral Liposomes Containing MAGE-1 and MAGE-3 DNA

MAGE-1 Gene Plasmid

MAGE-1 gene was cloned and isolated as described in Hoon, et al. *J. Immunol* (1995). The MAGE-1 gene was cloned into the pcDNA3 plasmid vector designed for expression of proteins in eukaryotic cells (InVitrogen, San Diego, Calif., USA). The pcDNA3 has an enhancer-promotor sequence from the immediate-early gene of the human cytomegalovirus, and a polyadenylation signal and transcription termination sequence from the bovine growth hormone gene. The MAGE-1 gene insert in pcDNA3 was verified by DNA sequencing. The pcDNA3 containing MAGE-1 gene (pMAGE-1) was purified by equilibrium ultracentrifugation using a CsCl-ethidium bromide gradient. Purified plasmid DNA was dissolved in 10 mM Tris-HCl, pH 8.0, 0.1 mM EDTA, assessed by spectrophotometry and shown to have an A260/A280 ratio of 1.9 or higher. Further analysis by gel electrophoresis was carried out to verify the purity of the purified plasmid.

Expression and Purification of rMAGE-1 rMAGE-1 was expressed as described in Hoon, et al. *J. Immunol* (1995) and purified by an affinity column containing $Ni^{2+}$-NTA resin (Qiagen, Chatsworth, Calif., USA). The rMAGE-1 construct was tagged at the amino terminal end with the sequence Gly-Ser-hexaHis for affinity purification and affinity ELISA. The recombinant protein was further purified by gel electrolution and a FPLC system (Bio-Rad, Richmond Calif., USA). Recombinant proteins were run in Laemmli 10% SDS-PAGE gel under reducing conditions.

MAGE-3 Gene Plasmid cDNA (942 bp) encoding full-length MAGE-3 was amplified by PCR from a human testis library (Clontech, Palo Alto, Calif., USA). The PCR cDNA product obtained was digested with restriction enzyme and the appropriate size fragment was subcloned into the vector pET30b (Novagen, Madison, Wis., USA) with hexaHis on the C-terminus, resulting in a plasmid designated pSH007. The full length MAGE-3 cDNA was sequenced by dideoxynucleotide sequencing method using T7 DNA polymerase (USB, Cleveland, Ohio, USA). Plasmid pSH007 was digested by EcoRV and NotI and the EcoRV-NotI fragment containing MAGE-3 gene was then inserted into the pcDNA3 plasmid. The pcDNA3 containing MAGE-3 gene (pMAGE-3) was purified and prepared as pMAGE-1.

Expression and Purification of rMAGE-3

A DNA fragment of the MAGE-3 gene with the terminal hexaHis affinity tag was removed from pSH007 and inserted into the SmaI site of pGEX-2t (Promega, Madison, Wis., USA). This expression plasmid was transformed into E. coli strain BL21 cells. Recombinant fusion protein was induced by isopropyl-D-thiogalactoside (IPTG) and purified from bacterial lysates by affinity chromatography using Glutathione Sepharose 4B (Pharmacia, Piscataway, N.J., USA). Before the elution of the fusion protein, rMAGE-3 was cleaved from the GST carrier by adding thrombin to the bound fusion protein and eluted off. The FPLC purified rMAGE-3 was verified by SDS-PAGE gel and Western blotting using $Ni^{2+}$-NTA conjugate (Qiagen), and then used for ELISA and Western blotting.

Preparation of HVJ-Liposomes

We prepared HVJ-liposomes encapsulating plasmid pcDNA3 containing MAGE-1 (pMAGE-1) or MAGE-3 (pMAGE-3) and HMG-1 protein. Preparation of HVJ-liposomes with plasmid DNA was carried out on the day or within 24 hours of injection into animals. The starting amount of plasmid DNA used in liposome encapsulation was 100 μg per tube. The amount of encapsulated plasmid DNA injected per animal was approximately 7–10 μg. This dose was the most efficient amount of HVJ-liposome DNA complex needed for in vivo gene expression. This was also the most logistically feasible dose of vector to produce a significant rapid and consistent immune response to the MAGE proteins. Optimization and control experiments with individual components of the fusigenic viral liposome of in vivo delivery of genes are described in Dzau, V. J., et al., Yanagihara, I, et al., and Kaneda, Y.

Briefly, HVJ (Z strain) was prepared from chorioallantoic fluid of virus inoculated embroyonated chick eggs and the hemagglutinating units (HAU) of the virus titer was determined by spectrophotometry. Preparation of liposomes involved mixing bovine brain L-α-phosphatidylserine sodium salt (Avanti Polar-lipids, Alabaster, Ala., USA), egg yolk L-α- phosphatidylcholine (Sigma, St. Louis, Mo., USA), and cholesterol (Sigma) in a glass tube at a weight ratio of 1:4.8:2 with tetrahydrofuran (Nakarai, Kyoto, Japan). The tube of lipid mixture was evaporated using a rotary evaporator while under 400 mm vacuum pressure and immersed in a 45° C. water bath. HMG-1 protein was purified from calf thymus as described in Kaneda, Y. 200 μg of purified plasmid DNA was mixed with 65 μg of HMG-1 and BSS (137 mM NaCl, 5.4 mM KCl, 10 mM Tris-HCl, pH 7.6) in nuclease-free tubes. The mixture was incubated in a water bath at 20° C. for one hour. The HMG-1 :DNA mixture was then added to the lipid mixture and agitated intensely by vortexing, water bath sonication and incubation in a 37° C. water bath for eight cycles. Balanced salt solution (BSS) was added to the unilamellar liposomes:HMG-1:DNA, incubated in a 37° C. shaking water bath and then put in an ice bath. Purified HVJ was inactivated with UV radiation 10 $J/m^2/s$ for three minutes. Inactivated HVJ (30,000 HAU) was added to the DNA:liposome solution, incubated on ice for 10 minutes and then incubated in a 37° C. shaking water bath for one hour. Free HVJ was then removed from HVJ-liposomes by sucrose density gradient centrifugation. HVJ-liposomes were then carefully removed from the density gradient, washed, precipitated by centrifugation (27,000 g, 30 minutes), resuspended in sterile BSS plus 2 mM $CaCl_2$ and kept on ice until used.

Immunization Protocol

The HVJ was treated with detergent, heat and UV light inactivating any pathogenic effects in the host. C57BL/6 male mice 6 to 8 weeks old in groups of three or four were used in each experiment. Mice were lightly anesthetized with ether vapor and injected (150 μl) with HVJ liposome solution in the right quadricep hind leg muscle only with a sterile 26 gauge needle syringe. Immunization of mice immediately after HVJ-liposome preparation was performed to obtain optimal results. Through experimentation an optimal vaccine immunization schedule was determined. Animals were immunized at various schedules: 3 times biweekly, 3 times weekly, or 2 times biweekly then monthly several times. No necrosis, inflammation or visible injury was observed after multiple injections at the same site. Groups of animals injected with plasmid DNA were kept for over 12 months and no visible injury or change in physical activity was observed compared with nonimmunized animals. The HVJ-liposome solution did not affect the well-being of the animals or hind leg function. Animals were bled before vaccination and at designated time points. Before bleeding animals were anesthetized using ether vapor and subsequently retro-orbital bled using sterile glass polished Pasteur pipettes. Blood (approximately 250 μl) was collected in 0.5 ml Eppendorf tubes, clotted at 4° C. and centrifuged at 700 g for 5 minutes. The serum was carefully removed and aliquoted into Eppendorf tubes and stored at −30° C. until used.

PCR and Southern Blot Analysis

Muscle biopsies were analyzed for the presence and expression of pcDNA3 and pMAGE-1 after selected periods of immunization. Tissue biopsies at the sites of vaccine injections were dissected out and nucleic acids were extracted. Total RNA and DNA from the tissue biopsies was extracted, isolated and purified using Tri-Reagent (Molecular Research Center, Cincinnati, Ohio, USA) protocol according to the manufacturer's instructions. RNA and DNA extraction was carried out in a designated sterile laminar flow hood with RNase and DNase-free labware. Purified RNA and DNA was quantified and assessed for purity by UV spectrophotometry.

RT-PCR and DNA PCR plus Southern blot analysis of MAGE-1 were performed as described in Hoon, et al., J. Clin. Oncol. (1995) PCR cDNA products of MAGE-1 were evaluated by gel electrophoresis on a 2% agarose gel and visualized by ethidium bromide staining under UV light. Southern blot analysis of gel electrophoresed PCR cDNA product was performed using a MAGE-1 specific cDNA probe. The pcDNA3, pMAGE-1, and MAGE-1 gene insert alone PCR cDNA products were 218 bp, 1136 bp and 920 bp, respectively. The sequences of the primers were as follows: pcDNA3: 5' primer was 5'-TAATACGACTCACTATAGGG-3'(SEQ ID NO:5) and the 3' ' primer was 5'-AGGGGCAAACAACAGATGGC-3' (SEQ ID NO:6) that gave a 218 bp cDNA product for pcDNA3 alone and a 1136 bp cDNA product for pcDNA3 with MAGE-1 insert.

Muscle biopsies of mice immunized with pcDNA3 alone were assessed 7, 14 and 28 days after immunization. Two mice from each time period were killed and assessed. A 218 bp RT-PCR and DNA PCR cDNA product was detected in all animals indicating the presence of pcDNA3. RT-PCR analysis of muscle biopsies of mice immunized with MAGE-1 vaccine was carried out on days 7 (two mice), 14 (three mice) and 28 (two mice) after immunization. All tissues examined were shown to express specific MAGE-1 mRNA 7, 14 and 28 days after immunization. MAGE-1 gene expression was further verified using a separate set of specific primers to MAGE-1 (RT-PCR cDNA product 920 bp). RT-PCR analysis of muscle biopsies at the site of MAGE-1 vaccine injection also showed the presence of the pcDNA 3 plasmid alone (218 bp). This may be due to incomplete transcription of the MAGE-1 gene insert in pcDNA3 or contamination of pcDNA3 without MAGE-1 gene insert in vector preparations. This was observed in only a few animals injected with different HVJ-liposome.

Normal muscle and other body organs (lung, kidney, liver) RNA from non-immunized animals of the same sex and age group were evaluated by RT-PCR and Southern blotting and were shown not to express MAGE-1 mRNA or plasmid pcDNA3 DNA.

Western Blotting

To assess the induction of anti-MAGE-1 and anti-MAGE-3-specific antibody responses after vaccination, 5 µg of recombinant human MAGE-1 (rMAGE-1) and recombinant human MAGE-3 (rMAGE-3) were produced as described above. Western blotting was carried out as described in Hoon, et al. *J. Immunol* (1995). Western blots with rMAGE-1 and rMAGE-3 were performed with sera of mice immunized at least twice to verify specificity of antibody responses. The blots were blocked with SuperBlock blocking buffer (Pierce, Rockford, Ill., USA) overnight at room temperature. Blots were tested with various mouse serum dilutions in PBS. After washing several times blots were incubated with alkaline phosphatase-conjugated goat anti-mouse IgG (γ-chain specific) or IgM (γ-chain specific) (Caltag, San Francisco, Calif., USA). Blots were washed and developed using 5-bromo-4-chloro-3-indolyl-1-phosphate and Nitro blue tetrazolium (Promega). Negative controls were conjugate alone with developing solution, non-immunized mice sera (age and sex matched), and pcDNA3 alone immunized mice.

Figure 2:
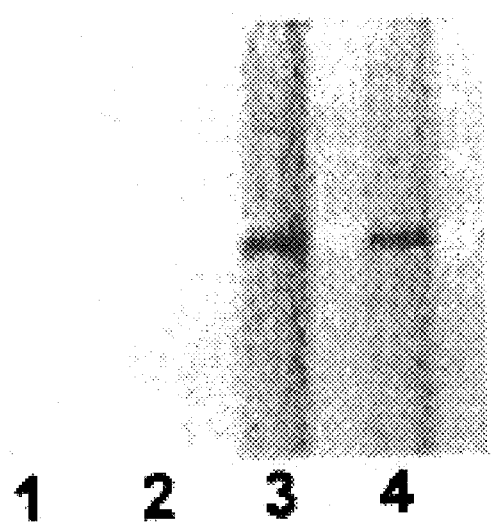
FIGS. 2(A and B) is an analysis of anti-MAGE-1 IgG (a) and anti-MAGE-3 IgG (b) in sera by Western blot. Lanes 1 and 2 show the results of the analysis on nonimmunized mice. Lanes 3 and 4 show the results of the analysis on mice immunized three times biweekly with either MAGE-1 or MAGE-3 vaccine.
Figure 2:
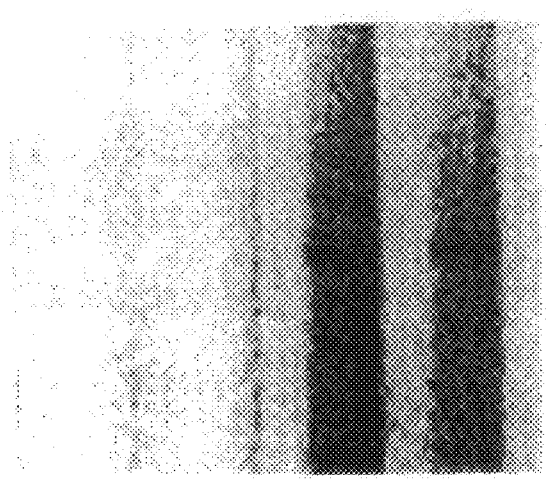

Results are shown in FIG. 2. No antibody (IgG) responses to rMAGE-1 or rMAGE-3 were detected in non-immunized mice. Mice immunized several times with HVJ-liposome complex containing pcDNA3 without a MAGE-1 or MAGE-3 insert also had no antigen-specific antibody response. Naked DNA given in vivo and taken up by cells degrades rapidly in lysosomes and endosomes. Mice immunized with MAGE-1 vaccine three times biweekly and assessed six weeks after immunization showed an induction of a strong antibody response to rMAGE-1. FIG. 2(*a*) (lanes 3 and 4). Similarly, mice immunized with MAGE-3 vaccine three times biweekly and followed-up after six weeks showed a strong antibody response to rMAGE-3. FIG. 2(*b*) (lanes 3 and 4). These studies indicated that antigen-specific IgG responses could be induced rapidly and maintained for at least eight weeks after immunization.

ELISA

Anti-MAGE-1 IgG antibodies were detected after immunization at various time-points by a MAGE-1 affinity ELISA. An anti-rMAGE-1 or -3 affinity ELISA was developed to detect mouse anti-MAGE-1 or -3 antibodies. Purified rMAGE-1 or rMAGE-3 (4 µg per well) with hexaHis tag in 10 mM Tris-HCl plus 50 mM NaCl buffered saline pH 7.5 (TBS) was incubated overnight at room temperature in $Ni^{2+}$ chelate coated ELISA microplates (Xenopore, Hawthorne, N.J., USA). Microplates were washed three times with TBS, incubated with 5% SuperBlock blocking buffer for two hours at room temperature and washed three times with PBS. Mouse serum was diluted in PBS and added to microwells and incubated at room temperature for two hours and subsequently washed three times with PBS. Goat anti-mouse IgG (γ-chain specific) horseradish peroxidase conjugate (Caltag, San Francisco, Calif., USA) was added and plates were incubated for two hours at room temperature, washed five times with PBS and developed with ortho-phenylenediamine sodium citrate solution plus 6 N HCl. Plates were then read at 490 nm by using an ELISA reader (Molecular Devices, Palo Alto, Calif., USA), and data were analyzed using the instrument software.

Figure 3:
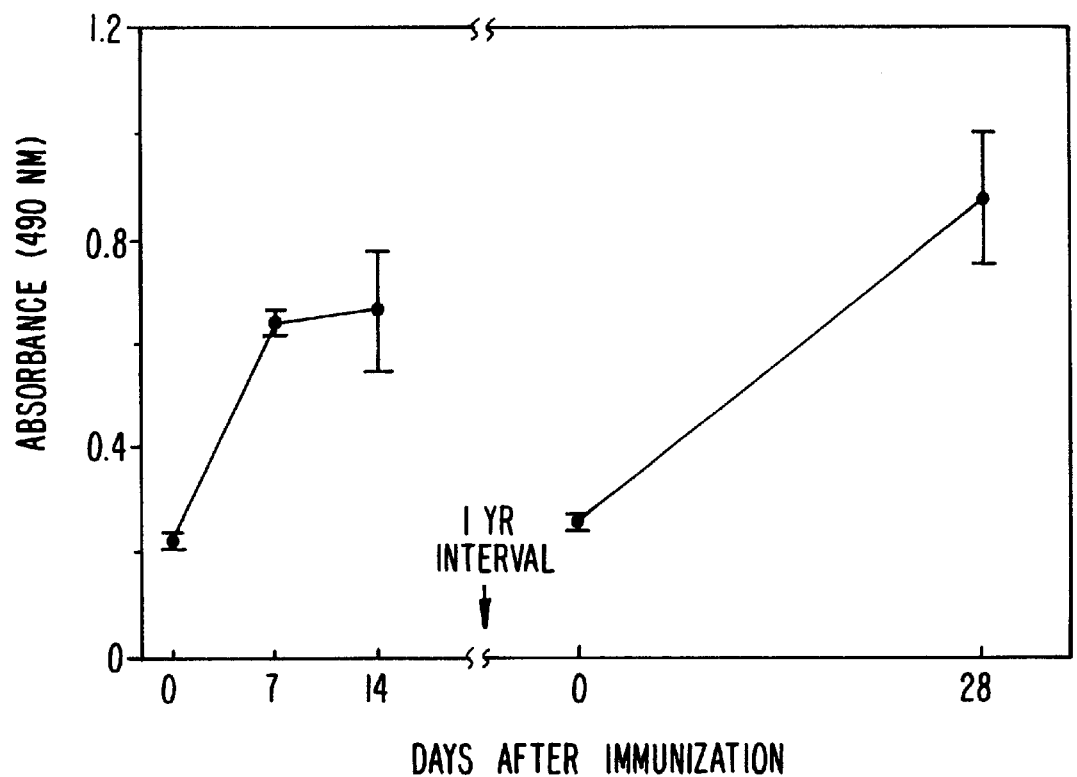
FIG. 3 is a chart showing the results of affinity ELISA with rMAGE-1 to detect IgG responses at 1:100 dilution of sera. Mean absorbency of triplicates +/− s.e. of all mice shown at specific time-points.

A representative experiment of antibody response after MAGE-1 immunization is shown in FIG. 3. Mice were immunized on day 1, 7, and 14, and then reimmunized approximately one year later. IgG antibody levels were enhanced after 7 days of booster immunization and maintained at day 14. Anti-MAGE-1 IgG antibody was induced and could be elevated with subsequent immunizations. Immunized mice were also assessed at different dilutions of serum ranging from 1:50 to 1:800. In general, after two immunizations on day 14 IgG anti-MAGE-1 antibody titers were 1/200 to 1/400. A positive antibody dilution was considered when it was 2 s.d. above negative serum background at a dilution of 1:100.

One year after three immunizations antibody levels went back down to background level as expected. Animals were reimmunized and evaluated after 4 weeks. Anti-MAGE-1 IgG responses were shown to be boosted to early immunization levels. These studies indicated that repeated immunization with the HVJ-liposome system does not induce any significant inhibiting immune response to the HVJ-liposome components or plasmid vector to prevent antigen-specific immunization.

EXAMPLE 2

MAGE-1 DT DNA Immunization

A plasmid containing MAGE-1 plus diphtheria toxin peptide DNA hybrid (MAGE-1 DT) was constructed to determine if genetically engineering an immunogenic determinant to MAGE-1 gene product would enhance antibody responses to MAGE-1. The complementary oligonucleotide sequences (sense: 5'AGCTTACGCAACCATTTCTTCAT-GACGGGTATGCTGTCAGTTGGAACACTGTT G-3' (SEQ ID NO:1); antisense: 5'TCGACAACAGTGTTC-CAACTGACAGCATACCCG CATGAAGAAATGGTTGCGTA-3'(SEQ ID NO:2)), derived from diphtheria toxin fragment B nucleotide sequence, corresponding to the C-terminal end 16 amino acid residue Thr Gln Pro Phe Leu His Asp Gly Tyr Ala Val Ser Trp Asn Thr Val (SEQ ID NO:3) were synthesized. The sequences were hybridized and inserted into the HindIII-SalI sites of pBluescript. cDNA encoding fall length of MAGE-1 was then inserted into BamHI-EcoRV sites, fusing it to the N-terminus of the DT peptide nucleotide sequence. The cDNA clone was sequenced by the dideoxynucleotide sequence method using T7 DNA polymerase (USB). The BamHI-XhoI fragment containing MAGE-1 DT gene was then inserted into the pcDNA3 plasmid. The plasmid MAGE-1 DT was purified as described in Example 1 for pMAGE-1.

Mice were immunized three times with MAGE-1 DT vaccine as described in Example 1.

The 16mer diphtheria toxin (DT) peptide sequence was tagged with a His tag to allow peptide affinity ELISA to be performed. The DT C-terminal peptide with a four histidine tag Thr Gln Pro Phe Leu His Asp Gly Tyr Ala Val Ser Trp Asn Thr Val His His His His (SEQ ID NO:4) was synthesized by Research Genetics (Huntsville, Ala., USA). The purity of the his tagged peptide used in the affinity ELISA was greater than or equal to 97%. The peptide (100 pmoles per well) was incubated in $Ni^{2+}$ chelate coated ELISA microplates. Procedures for ELISA were as described in Example 1. Rabbit anti-DT peptide serum ($1:10^4$ dilution) was used as a positive control for DT-His tag peptide binding in the affinity ELISA plates.

The antibody response to rMAGE-1 assessed by Western blot after immunization with MAGE-1 DT vaccine immunization. In assessment of mice immunized with MAGE-1 DT by affinity ELISA there was some enhancement (not significant) of antibody response to DT peptide above control MAGE-1 vaccine. Overall, adding a second immunogenic determinant did show some improvement in antibody responses to rMAGE-1, but it was not significant. However, increasing the length of the peptide sequence should generate a cellular immune response. In addition, adding a peptide sequence with an anchoring motif to HLA molecules should enhance this response. Longer initial peptide sequences also will increase antibody induction.

EXAMPLE 3

LACZ RNA Expression in BHK-21 Cells After Transfer by Viral Liposomes

Figure 4:
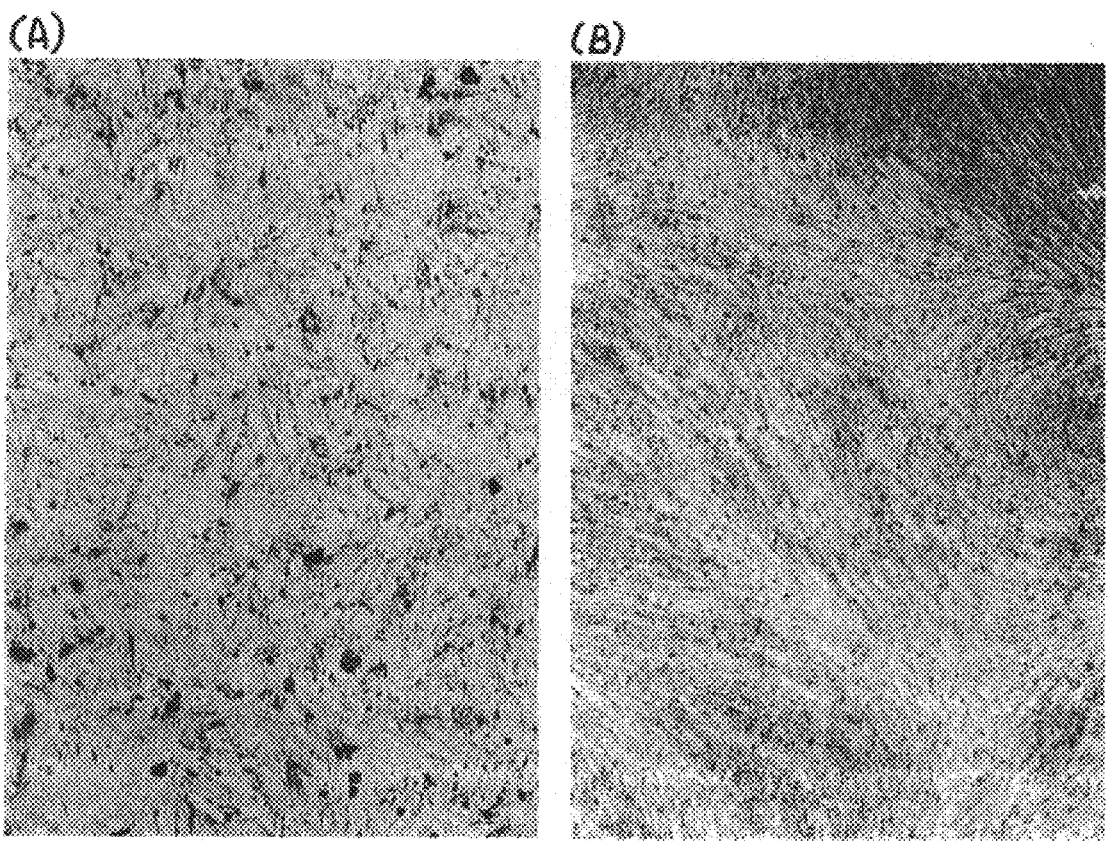
FIGS. 4(A and B) shows lacZ RNA expression in BHK-21 cells at 24 hours after the transfer by viral liposomes containing in vitro translated RNA (A) or TE buffer without RNA (B).

BHK-21 cells were incubated with viral liposomes containing in vitro transcribed RNA for pSFV3-lacZ. LacZ RNA expression in the BHK-21 cells at 24 hours after the transfer of viral liposomes is shown in FIG. 4(A). As a control, RNA expression after the transfer of TE buffer with RNA is shown in FIG. 4(B). More than 80% of BHK-21 cells were stained blue by X-gal staining. FIG. 4(A). No blue staining was obtained in control experiment. FIG. 4(B).

In vitro RNA Synthesis by pSFV Expression Vector pSFV3-lacZ DNA (10 $\mu$g)(GIBCO BRL, Tokyo, Japan) was linearized with Spe I, purified by ethanol precipitation after phenol extraction, and suspended in TE (10 mM Tris-Cl, 1 mM EDTA, pH 8.0) to 0.6 $\mu$g/ml. The following materials when then mixed in a 1.5 ml tube:

20 $\mu$l NTP mix (2.5 mM ATP, 2.5 mM CTP, 2.5 mM UTP, 1.25 mM GTP)

10 $\mu$l 5×SP6 buffer

5 $\mu$l 10 mM RNA Capping Analog

5 $\mu$l 10 mM DTT (mix after adding)

5 $\mu$l RNase inhibitor (RNasin)

2.5 $\mu$l linearized pSFV3-lacZ 2.5 $\mu$l Sp6 RNA polymerase for a total volume of 50 $\mu$l. The materials were from GIBCO BRL, Tokyo, Japan, except RNasin and SP6 RNA polymerase, which were from Promega Corp., Madison, Wis., USA. The mixture was incubated at 37° C. for one hour. In vitro transcribed RNA was examined by 0.5% agarose gel electrophoresis. The RNA was purified by isopropanol precipitation and resuspended in TE. The amount was then estimated based on absorbance at 260 nm. Usually more than 20 $\mu$g of RNA was obtained in each reaction.

Transfer of RNA to BHK-21 Cells

20 $\mu$g of in vitro transcribed RNA for pSFV-lacZ were incorporated into liposomes of phosphatidylcholine, cholesterol and DC-cholesterol. Saeki, Y., et al. The liposomes were fused with UV-inactivated HVJ as described in Example 1 to form HVJ-cationic liposomes. After sucrose-gradient centrifugation at 62,800 g for 90 minutes, one tenth of the HVJ-liposome suspension was added to BHK-21 cells in a 100 mm dish (60–70% confluent). Cells were incubated with the liposome suspension in the presence of Dulbecco's medium MEM containing 10% fetal calf serum for 30 minutes at 37° C. The culture medium was changed and replaced with new culture medium. Cells were cultured for 24 hours in a 5% $CO_2$ incubator at 37° C. and then fixed with 1% glutaraldehyde. The cells were stained with X-gal solution at 37° C. for 2–16 hours as described in Mercer, et al.

EXAMPLE 4

Figure 5:
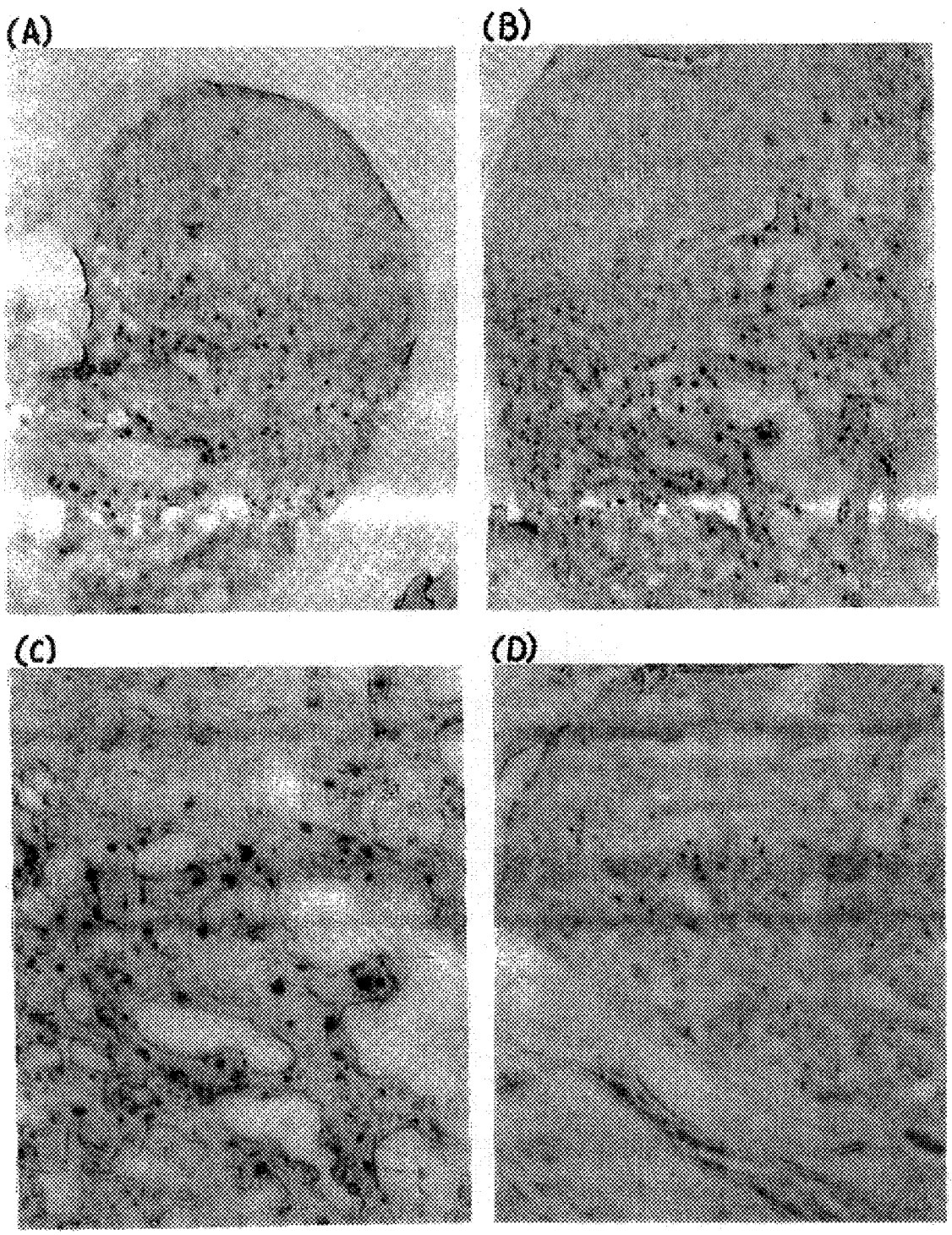
FIGS. 5(A–D) shows lacZ RNA expression in mouse skeletal muscle on days 3 (A), 5 (B and C), and 9 (D) after the transfer by viral liposomes containing in vitro translated RNA. C is a higher magnification view of B.

LACZ RNA Expression in Mouse Skeletal Muscle After RNA Vaccination by Viral Liposomes Viral liposomes containing in vitro transcribed RNA for pSFV-lacZ were injected into mouse skeletal muscle on days 1, 3, 5, 7, and 9. Expression of lacZ RNA on day 3 is shown in FIG. 5(A). RNA expression on day 5 is shown in FIGS. 5(B) and 5(C). RNA expression on day 9 is shown in FIG. 5(D).

In vitro RNA Synthesis by pSFV Expression Vector

RNA was synthesized in vitro as described in Example 3.

Transfer of RNA to Mouse Skeletal Muscle

300 $\mu$g of in vitro transcribed RNA for pSFV3-lacZ were incorporated in AVE-liposomes as described in Saeki, Y., et al. The liposomes were fused with UV-inactivated HVJ as described in Example 1 to form HVJ-AVE liposomes. After sucrose-gradient centrifugation at 62,800 g for 90 minutes, the HVJ-AVE liposome suspension was diluted four times with BSS (10 mM Tris-Cl, pH 7.5, 137 mM NaCl, 5.4 mM KCl). The solution was then concentrated by centrifugation at 27,800 g for 30 minutes. The pellet of HVJ-AVE liposomes was resuspended in 300 $\mu$l of BSS containing 1 mM $CaCl_2$. 15 $\mu$l of HVJ-AVE liposome suspension was injected into each of four sites of the hind leg muscle of individual C57/BL6 8 week old male mice, for a total of 60 $\mu$l of suspension. On days 1, 3, 5, 7, and 9, the mouse was anesthetized by pentobarbital, and the skeletal muscle around the injected sites was prepared for histopathological examination. The sample was fixed in 1% glutaraldehyde, immersed in 20% sucrose solution, and embedded in OCT fixing compound. A 10 $\mu$m frozen tissue section [slice] of the muscle was prepared and stained in 0.1% X-gal solution at 37° C. for 16 hours as described in Example 3.

EXAMPLE 5

Preparation of AVE-Liposomes (Artificial Viral Envelope) and HVJ-DC-Liposome

AVE-liposomes (artificial viral envelope) and cationic HVJ-liposomes containing DC-cholesterol (3beta[N',N'- dimethylaminomethane)-carbamoyl]-cholesterol) were prepared as described in Saeki and Kaneda, Protein-modified liposomes (HVJ-liposomes) for the delivery of genes, oligonucleotides and proteins. *Cell biology, a laboratory* handbook (2d ed.) edited by J. E. Celis; Academic Press Inc., San Diego) vol. 4, 123–130 (1998) with modifications as described below.

A mixture for positively charged DC-cholesterol liposome contained cholesterol egg phosphatidylcholine, and DC-chol at the molar ratio of 4:5:1. The lipid composition of AVE liposome was phosphatidylserine:egg phosphatidylcholine:dioleoylphosphatidylethanolamine:sp hingomyelin:cholesterol=10:13.3:13.3:13.3:50 at the molar ratio. Liposomes were prepared by hydrating and agitating these lipid mixtures with 200 ml of balanced salt solution. Each lipid was dissolved in chloroform at the concentration of 30 mM. Lipid mixtures were prepared by mixing lipid solutions in various combinations. 500 $\mu$l (15 $\mu$mole) of each lipid mixture was transferred into a glass tube and dried as a thin lipid film by evaporation. The dried lipid mixture was hydrated in 200 $\mu$l of balanced salt solution (BSS; 137 mM NaCl., 5.4 mM KCl, 10 mM Tris-HCl, pH 7.6) containing DNA, RNA, oligonucleotides or protein, which were entrapped by dispersion in the aqueous phase at 37° C. The mixture was agitated intensely by vortexing for 30 seconds and then left to stand for 30 seconds. This procedure was repeated eight times. 800 $\mu$l of BSS was added to the tube, the liposomes suspension was extruded through a cellulose acetate membrane filter (pore size: 0.45 $\mu$m), and the liposomes left in the filter were collected by extruding 500 $\mu$l of BSS. The 1.5 ml of liposome solution and then 500 $\mu$l of BSS was extruded through another membrane filter with 0.20 $\mu$m pores to obtain sized unilamellar liposomes (2 ml in total).

The liposome suspension prepared above (2 ml, composed of 15 $\mu$mole of lipid) was mixed with 1 ml of HVJ suspension [30,000 hemagglutinating units (HAU)] and incubated at 37° C. for one hour with shaking (120/min) in a water bath. The HVJ-liposome complexes were then separated from free HVJ by sucrose density gradient centrifugation. The mixture was layered onto a discontinuous sucrose gradient (1 ml of 50% and 6.5 ml of 30% sucrose in BSS) and centrifuged at 62,800 g at 4° C. for 1.5 hours in a swing bucket rotor. Then the HVJ-liposomes were visualized in a layer between BSS and 30% sucrose solution, and free HVJ was sedimented in a layer between 30% and 50% sucrose solution. We collected HVJ-liposomes using a pasteur pipet into a sterilized tube. The volume of HVJ-liposomes was usually about 0.5 ml, and the total volume was adjusted to 1 ml with BSS.

EXAMPLE 6

Figure 6:
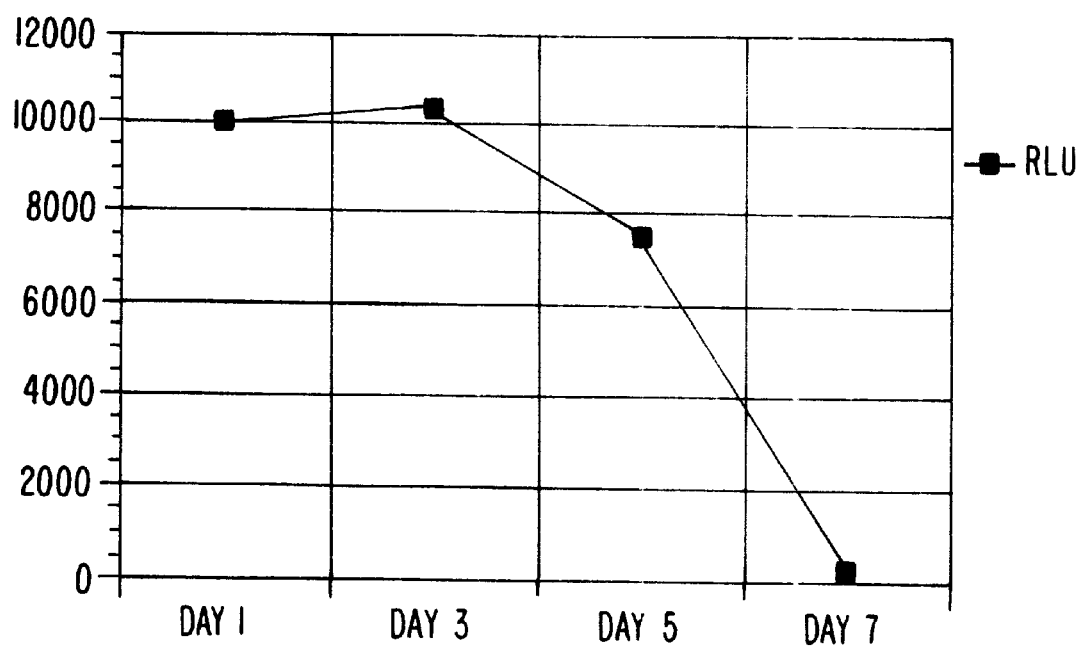
FIG. 6 shows lacZ RNA expression in spleen after injection of in vitro synthesized lacZ RNA using HVJ-DC-liposome.

LACZ RNA Expression in Mouse Spleen After RNA Vaccination by HVJ-DC-Liposome 300 $\mu$g of LacZ RNA synthesized by pSFV3-lacZ vector system was incorporated into HVJ-DC-liposome (cationic type). One-tenth (50 $\mu$l) of HVJ-DC-liposome solution (total 500 $\mu$l) was directly injected into spleen of C57/BL6 mouse. The mice were sacrificed on day 1, 3, 5 and 7 after injection. The spleen was isolated, washed with PBS twice, and lysed with 300 $\mu$l of detergent lysis buffer. 40 $\mu$l of each extract was assayed for LacZ activity using a Luminecent beta-gal Detection Kit II (Clontech). The signal was detected by a tube luminometer (Lumat LB 9507; Bertold). Each value in FIG. 6 is the mean of duplicate samples.

The highest LacZ activity was obtained on day 1 and 3, then decreased by 25% of the highest value, and finally the activity was not detected on day 7 after the transfer. FIG. 6.

The present invention is not to be limited in scope by the exemplified embodiments which are intended as illustrations of single aspects of the invention, and methods which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims.

All references cited within the body of the instant specification are hereby incorporated by reference in their entirety.

REFERENCES

Autran, B., et al., "Monoclonal B-cell Response to Diphtheria Toxoid: Evidence for Cross-Reactive Epitopes," *Immunol.* (1987); 60: 531–538.

Cheung, I., and Cheung, N-K, "Molecular Detection of Gage Expression in Peripheral Blood and Bone Marrow: Utility as Tumor Marker for Neuroblastoma," *Clin. Cancer Res.*, 3, 821–826 (1997).

Conry, R. M., et al. "Characterization of a Messenger RNA Polynucleotide Vaccine Vector," *Cancer Res.* (1995); 55: 1397–1400.

De Plaen, E. et al., "Structure, Chromosomal Localization, and Expression of 12 Genes of the MAGE Family," *Immunogenetics* (1994); 40: 360–369.

Doi, F., Chi, D., Charuworn, B. B., Conrad, A., Russell, J., Morton, D. L., and Hoon, D. S. B., "Detection of B-human Chorionic Gonadotropin mRNA as a Maker for Cutaneous Malignant Melanoma," *Int. J. Cancer*, 65, 454–459 (1996).

Dzau, V. J.; Mann, M. J.; Morishita, R.; Kaneda Y., "Fusigenic Viral Liposome for Gene Therapy in Cardiovascular Diseases," *Proc. Nat'l Acad. Sci. USA* (1996); 93: 11421–11425.

Eynde, B., Peeters, O., Backer, O., Gaugler, B., Lucas, S., and Boon, T., "A New Family of Genes Coding for an Antigen Recognized by Autologous Cytolytic T Lymphocytes on a Human Melanoma," *J. Exp. Med.*, 182, 689–698 (1995)

Gerhard, M., Juhl, H., Kalthoff, H., Schreiber, H., Wagener, C., and Neumaier, M., "Specific Detection of Carcinoembryonic Antigen-expressing Tumor Cells in Bone Marrow Aspirates by Polymerase Chain Reaction," *J. Olin. Oncol.*, 12, 725–729 (1994).

Gomella, L. G. Raj, G. V., and Moreno, J. G., "Reverse Ttranscriptase Polymerase Chain Reaction for Prostate Specific Antigen in the Management of Prostate Cancer," *J. Urology*, 158, 326–337 (1997).

Graham, R. A.; Burchell, J. M.; Beverly, P.; Taylor-Papadimitriou J., "Intramuscular Immunization with MUC1 cDNA Can Protect C37 Mice Challenged with MUC1-Expressing Syngeneic Mouse Tumor Cells," *Int. J. Cancer* (1996); 65: 664–670.

Hoon, D. S. B., et al., "Detection of Occult Melanoma Cells in Blood with a Multiple-Marker Polymerase Chain Reaction Assay," *J. Clin. Oncol.* (1995); 13: 2109–2116.

Hoon, D. S. B., Irie, R. F., "Current Status of Human melanoma Vaccines: Can They Control Malignant Melanoma? *BioDrugs*, 7, 66–84 (1997).

Hoon, D. S. B., Irie, R. F., "Current Status of Melanoma Vaccines. Can They Control Malignant Melanoma?" *BioDrug* (1997); 1: 66–84.

Hoon, D. S. B., Sarantou, T., Doi, F., Chi, D., Kuo, C., Conrad, A., Schmid, P., Turner, R., and Guiliano, A., "Detection of Metastic Breast Cancer by B-hCG Polymerase Chain Reaction," *Int. J. Cancer*, 69, 369–374 (1996).

Hoon, D. S. B., Yuzuki D.; Hayashida M.; Morton, D. L., "Melanoma Patients Immunized with Melanoma Cell Vaccine Induce Antibody Responses to Recombinant MAGE-1 Antigen," *J. Immunol* (1995) 154: 730–737.

Huygen, K., et al., "Immunogenicity and Protective Efficacy of a Tuberculosis DNA Vaccine," *Nature Med* (1996); 2: 893–898.

Kaneda, Y., "Virus (Sendai Virus Envelope)-Mediated Gene Transfer," *Cell Biology: A Laboratory Handbook,* Academic Press, San Diego (1994), pp. 50–57.

Kawakami, Y., Eliyau, S., Delgado, CH., et al, "Cloning of the Gene Coding for a Shared Human Melanoma Antigen Recognized by Autologous T cells Infiltrating into Tumour," *Proc. Natl. Acad. Sci., USA,* 91, 3515–3519 (1994).

Kwon, S. K., "Pigmentation genes: The Tyrosinase Gende Family and the Pmel 17 Gene Family," *J. Invest. Dermatol.,* 100, 134S–140S, (1993).

Mercer, E. H., et al., *Neuron* (1991); 7: 703–716.

Michel, M. L., et al., "DNA-Mediated Immunization to the Hepatitis B Surface Antigen in Mice: Aspects of the Humoral Response Mimic Hepatitis B Viral Infection in Humans," *Proc. Nat'l Acad. Sci USA* (1995); 92: 5307–5311.

Mivechi, N. F., and Rossi, J. J., "Use of Polymerase Chain Reaction to Detect the Expression of the Mr 70,000 Heat Shock Genes in Control or Heat Shock Leukemic Cells as Correlated to Their Heat Response," *Cancer Res.,* 50, 2877–2884 (1990).

Nollau, P., Moser, C., Weinland, G., and Wagener, C., "Detection of K-Ras Mutations in Stools of Patients with Colorectal Cancer by Mutant-enriched PCR," *Int. J. Cancer,* 66, 332–336 (1996).

Ralhan, R., and Kaur, J., "Differential Expression of Mr 70,000 Heat Shock Protein in Normal Premalignant, and Malignant Human Uterine Cervix," *Clin. Cancer Res.,* 1, 1217–1222 (1995).

Saeki, Y., et al., *Hum. Gene Ther.* (1997); 8: 2133–2141.

Sarantou, T., Chi, D., Garrison, D., Conrad, A., Schmid, P., Morton, D. L., and Hoon, D. S. B., "Melanoma-Associated Antigens as Messenger RNA Detection Markers for Melanoma," *Cancer Re.,* 57, 1371–1376 (1997).

Sensi, M., Traversari, C., Radrizzani, M., Stefania, S., Maccalli, C., Mortarini, R., Rivoltini, L., Faina, C., Nicolini, G., Wlofel, T., Brichard, V., Boon, T., Bordignon, C., Anichini, A., and Parmiani, G., "Cytotoxic T-lymphocyte Clones from Different Patients display Limited T-cell-receptor Variable-region Gene Usage in HLA-A2 Restricted Recognition of the Melanoma Antigen Melan-A/ Mart 1," *Proc. Natl. Acad. Sci.,* USA, 92, 5674–5678 (1995).

Shirasawa, S., Furuse, M., Yokoyama, N., Sasazuki, T., "Altered Growth of Human Colon Cancer Cell lines Disrupted at Activated Ki-Ras," *Science,* 260, 85–88 (1993).

Takahashi, T., Irie, R., Morton, D. L., and Hoon, D. S. B., "Recognition if gp43 Tumor-associated Antigen Peptide by Both HLA-A2 Restricted CTL Lines and Antibodies from Melanoma Patients," *Cell. Immunol.,* 178, 162–171 (1997).

Vijayasaradhi, S., Bouchard, B., and Houghton, A. N. "The melanoma Antigen gp75 is the Human Homologue of the Mouse b (brown) Locus Gene Product," *J. Exp. Med.,* 171, 1375–1380 (1990).

Wang, B., et al., "Gene Inoculation Generates Immune Responses Against Human Immunodeficiency Virus Type 1," *Proc. Nat'l Acad. Sci. USA* (1993); 90: 4156–4160.

Wolf, J. A., et al., "Long-Term Persistence of Plasmid DNA and Foreign Gene Expression in Mouse Muscle," *Hum. Mol. Genet. (*1992); 1: 363–369.

Wolfel, T., Van Pel A., Brichard V., et al., "Two Tryosinase Nonapeptides Recognized on IILA-A2 melanoma by Autologous Cytolytic T lymphocytes," *Eur J. Immunol.,* 24, 759–764 (1994).

Yanagihara, I., et al., "Expression of Full-Length Human Dystrophin cDNA in MDX Mouse Muscle by HVJ-Liposome Injections," *Gene Therapy* (1996); 3: 549–553.

Yokoyama, K., Yasumoto, K., Suzuki, H., and Shibahara, S., "Cloning of the Human DOPAchrome Tautomerase/ tyrosinase-realted Protein 2 Gene Identification of Two Regulatory Regions Required for its Pigment Cell-specific Expression," *J. Biol, Chem.,* 269, 27080–27087 (1994).

Yoshino, I., Goedegebuure, P., Peoples, G., Lee, K-Y., and Eberlein, T., "Human Tumor-infiltrating CD4+ T Cells React to B Cell Lines Expressing Heat Shock Protein 70," *J. Immunol.,* 153, 4149–4158 (1994).

Zhang, Y., Zippe, C., Van Lente, F., Klein, J., and Gupta, M., "Combined Nested Reverse Transcription-per Assay for Prostate-specific Antigen and Prostate-specific Membrane Antigen in Detecting Circulating Prostatic Cells," *Clin. Cancer Res.,* 3, 1215–1220 (1997).

What is claimed is:

1. A vaccine comprising, in an amount effective upon administration to a mammal to suppress or attenuate the growth of a melanoma tumor comprising a melanoma-associated antigen, viral liposomes comprising a fusigenic HVJ polypeptide and an mRNA encoding the melanoma-associated antigen, wherein the mRNA is translated in vivo upon such administration to produce the melanoma-associated antigen.

2. The vaccine of claim 1, further comprising HMG-1.

3. The vaccine of claim 1, further comprising a protein that directs protein or RNA trafficking in the cytoplasm of cells.

4. The vaccine of claim 1, wherein the viral liposomes comprise mRNA encoding more than one melanoma-associated antigen.

5. The vaccine of claim 1, further comprising mRNA encoding a second immunogenic peptide.

6. The vaccine of claim 1, wherein the melanoma-associated antigen is MAGE-1.

7. The vaccine of claim 1, wherein the melanoma-associated antigen is MAGE-3.

8. The vaccine of claim 1, wherein the melanoma-associated antigen is gp100.

9. The vaccine of claim 1, wherein the melanoma-associated antigen is TRP-2.

10. The vaccine of claim 1, wherein the melanoma-associated antigen is tyrosinase.

11. The vaccine of claim 1, wherein the melanoma-associated antigen is MART-1.

12. The vaccine of claim 1, wherein the melanoma-associated antigen is HSP-70.

13. The vaccine of claim 1, wherein the melanoma-associated antigen is β-HCG.

14. A method for immunizing against a tumor-associated antigen, the method comprising the step of administering viral liposomes comprising a fusigenic HVJ polypeptide and an mRNA encoding the tumor-associated antigen wherein the mRNA is translated in vivo upon such administration to produce the tumor-associated antigen.

15. The method of claim 14, wherein the viral liposomes further comprise HMG-1.

16. The method of claim 14, wherein the viral liposomes comprise mRNA encoding more than one tumor-associated antigen.

17. The method of claim 14, wherein the viral liposomes further comprise an mRNA encoding a second immunogenic peptide.

18. The method of claim 14, wherein the tumor-associated antigen is MAGE-1.

19. The method of claim 14, wherein the tumor-associated antigen is MAGE-3.

20. The method of claim 14, wherein the tumor-associated antigen is gp100.

21. The method of claim 14, wherein the tumor-associated antigen is TRP-2.

22. The method of claim 14, wherein the tumor-associated antigen is tyrosinase.

23. The method of claim 14, wherein the tumor-associated antigen is MART-1.

24. The method of claim 14, wherein the tumor-associated antigen is HSP-70.

25. The method of claim 14, wherein the tumor-associated antigen is β-HCG.

26. The method of claim 14, wherein the viral liposomes are administered subcutaneously.

27. The method of claim 14, wherein the viral liposomes are administered into a muscle.

28. The method of claim 14, wherein the viral liposomes are administered into an organ.

29. The method of claim 14, wherein the viral liposomes are administered intradermally.

30. The method of claim 14, wherein the tumor-associated antigen is expressed by a host normal cell.

31. A method of treating melanoma, the method comprising the step of administering viral liposomes comprising a fusigenic HVJ polypeptide and an mRNA encoding a melanoma-associated antigen.

32. The method of claim 31, wherein the viral liposomes further comprise HMG-1.

33. The method of claim 31, wherein the viral liposomes further comprise a protein that directs protein or RNA trafficking in the cytoplasm of cells.

34. The method of claim 31, wherein the viral liposomes comprise mRNA encoding more than one melanoma-associated antigen.

35. The method of claim 31, wherein the viral liposomes further comprise an mRNA encoding a second immunogenic peptide.

36. The method of claim 31, wherein the melanoma-associated antigen is MAGE-1.

37. The method of claim 31, wherein the melanoma-associated antigen is MAGE-3.

38. The method of claim 31, wherein the melanoma-associated antigen is gp100.

39. The method of claim 31, wherein the melanoma-associated antigen is tyrosinase.

40. The method of claim 31, wherein the melanoma-associated antigen is MART-1.

41. The method of claim 31, wherein the melanoma-associated antigen is HSP-70.

42. The method of claim 31, wherein the melanoma-associated antigen is β-HCG.

43. The method of claim 31, wherein the viral liposomes are administered subcutaneously.

44. The method of claim 31, wherein the viral liposomes are administered into a muscle.

45. The method of claim 31, wherein the viral liposomes are administered into an organ.

46. The method of claim 31, wherein the melanoma-associated antigen is expressed by a host normal cell.

47. A method of inducing an antibody response, the method comprising the step of administering viral liposomes comprising a fusigenic HVJ polypeptide and an mRNA encoding a tumor-associated antigen wherein the mRNA is translated in vivo upon such administration to produce the tumor-associated antigen.

48. The method of claim 47, wherein the viral liposomes further comprise HMG-1.

49. The method of claim 47, wherein the viral liposomes further comprise a protein that directs protein or RNA trafficking in the cytoplasm of cells.

50. The method of claim 47, wherein the viral liposomes comprise mRNA encoding more than one tumor-associated antigen.

51. The method of claim 47, wherein the viral liposomes further comprise mRNA encoding a second immunogenic peptide.

52. The method of claim 47, wherein the tumor-associated antigen is MAGE-1.

53. The method of claim 47, wherein the tumor-associated antigen is MAGE-3.

54. The method of claim 47, wherein the tumor-associated antigen is gp100.

55. The method of claim 47, wherein the tumor-associated antigen is TRP-2.

56. The method of claim 47, wherein the tumor-associated antigen is tyrosinase.

57. The method of claim 47, wherein the tumor-associated antigen is MART-1.

58. The method of claim 47, wherein the tumor-associated antigen is HSP-70.

59. The method of claim 47, wherein the tumor-associated antigen is β-HCG.

60. The method of claim 47, wherein the viral liposomes are administered subcutaneously.

61. The method of claim 47, wherein the viral liposomes are administered into a muscle.

62. The method of claim 47, wherein the viral liposomes are administered into an organ.

63. The method of claim 47, wherein the tumor-associated antigen is expressed by a host normal cell.

64. A method of inducing a cell mediated immune response, the method comprising the step of administering viral liposomes comprising a fusigenic HVJ polypeptide and an mRNA encoding a tumor-associated antigen wherein the mRNA is translated in vivo upon such administration to produce the tumor-associated antigen.

65. The method of claim 64, wherein the viral liposomes further comprise HMG-1.

66. The method of claim 64, wherein the viral liposomes further comprise a protein that directs protein or RNA trafficking in the cytoplasm of cells.

67. The method of claim 64, wherein the viral liposomes comprise mRNA encoding more than one tumor-associated antigen.

68. The method of claim 64, wherein the viral liposomes further comprise mRNA encoding a second immunogenic peptide.

69. The method of claim 64, wherein the tumor-associated antigen is MAGE-1.

70. The method of claim 64, wherein the tumor-associated antigen is MAGE-3.

71. The method of claim 64, wherein the tumor-associated antigen is gp100.

72. The method of claim 64, wherein the tumor-associated antigen is TRP-2.

73. The method of claim 64, wherein the tumor-associated antigen is tyrosinase.

74. The method of claim 64, wherein the tumor-associated antigen is MART-1.

75. The method of claim 64, wherein the tumor-associated antigen is HSP-70.

76. The method of claim 64, wherein the tumor-associated antigen is β-HCG.

77. The method of claim 64, wherein the viral liposomes are administered subcutaneously.

78. The method of claim 64, wherein the viral liposomes are administered into a muscle.

79. The method of claim 64, wherein the viral liposomes are administered into an organ.

80. The method of claim 64, wherein the tumor-associated antigen is expressed by a host normal cell.

81. The method of claim 31, wherein the melanoma-associated antigen is TRP-2.

82. The vaccine of claim 1, wherein the polypeptide is recombinantly produced.

83. The vaccine of claim 1, wherein the polypeptide is obtained from an inactivate viral preparation.

84. The vaccine of claim 1, wherein the viral liposomes further comprise cationic lipids.

85. The vaccine of claim 1, wherein the viral liposomes further comprise anionic lipids.

86. The vaccine of claim 1, wherein the viral liposomes further comprise AVE.

87. The vaccine of claim 1, wherein the mRNA is synthesized from a pSFV3 vector.

* * * * *